(12) United States Patent
Hermes

(10) Patent No.: US 6,476,910 B1
(45) Date of Patent: Nov. 5, 2002

(54) LIGHT SCATTERING APPARATUS AND METHOD FOR DETERMINING RADIATION EXPOSURE TO PLASTIC DETECTORS

(75) Inventor: Robert E. Hermes, White Rock, NM (US)

(73) Assignee: The Regents of the University of California, Oakland, CA (US)

( * ) Notice: Subject to any disclaimer, the term of this patent is extended or adjusted under 35 U.S.C. 154(b) by 167 days.

(21) Appl. No.: 09/650,776

(22) Filed: Aug. 29, 2000

(51) Int. Cl.$^7$ .......................... G01N 15/02; G01N 15/06
(52) U.S. Cl. .................... 356/336; 356/443; 356/239.1; 250/573; 250/574
(58) Field of Search ................................ 356/336, 443, 356/444, 446, 239.1, 239.7, 30; 250/216, 553, 573, 574

(56) References Cited

U.S. PATENT DOCUMENTS

| | | | | |
|---|---|---|---|---|
| 4,163,154 A | * | 7/1979 | Wheeler et al. | 250/473 |
| 4,381,454 A | * | 4/1983 | Griffith et al. | 250/472.1 |
| 4,383,179 A | * | 5/1983 | Eisen et al. | 250/472.1 |
| 4,925,298 A | * | 5/1990 | Dobrilla | 356/30 |
| 5,008,542 A | * | 4/1991 | Look et al. | 250/341 |
| 5,117,120 A | * | 5/1992 | Margaliot et al. | 250/572 |
| 5,870,188 A | | 2/1999 | Ozaki et al. | |
| 5,981,949 A | * | 11/1999 | Leahy et al. | 250/332 |
| 6,388,745 B2 | * | 5/2002 | Stevens et al. | 356/239.7 |

OTHER PUBLICATIONS

"Annalen Der Physik," 10 pages, Greifswal, Physikalisches Institute; (Jan. 7, 1908) No translation available.

Groetz, J. E. et al.; "A New Method for Reading CR–39 by Using Coherent Light Scattering," Radiation Protection Dosimetry, (1999), vol. 85, Nos. 1–4, at pp. 447–450.

Levi, Leo; "Basics of Atmospheric Scattering," at pp. 90–93; Appendix 12.1: "Rayleigh and MIE Scattering," at pp. 136–143, Applied Optics, John Wiley & Sons, Inc. (1980), New York, New York.

Parker, Sybil P., (Editor in Chief) "Light Scattering Photometry," at pp. 70–72, Encyclopedia of Science & Technology, McGraw–hill (1997) 8th Edition, New York New York.

(List continued on next page.)

*Primary Examiner*—Frank G. Font
*Assistant Examiner*—Roy M. Punnoose
(74) *Attorney, Agent, or Firm*—John P. O'Banion

(57) ABSTRACT

An improved system and method of analyzing cumulative radiation exposure registered as pits on track etch foils of radiation dosimeters. The light scattering apparatus and method of the present invention increases the speed of analysis while it also provides the ability to analyze exposure levels beyond that which may be properly measured with conventional techniques. Dosimeters often contain small plastic sheets that register accumulated damage when exposed to a radiation source. When the plastic sheet from the dosimeter is chemically etched, a track etch foil is produced wherein pits or holes are created in the plastic. The number of these pits, or holes, per unit of area (pit density) correspond to the amount of cumulative radiation exposure which is being optically measured by the apparatus. To measure the cumulative radiation exposure of a track etch foil a high intensity collimated beam is passed through foil such that the pits and holes within the track etch foil cause a portion of the impinging light beam to become scattered upon exit. The scattered light is focused with a lens, while the primary collimated light beam (unscattered light) is blocked. The scattered light is focused by the lens onto an optical detector capable of registering the optical power of the scattered light which corresponds to the cumulative radiation to which the track etch foil has been exposed.

26 Claims, 9 Drawing Sheets

OTHER PUBLICATIONS

Parker, Sybil P., (Editor in Chief) "Scattering of Electromagnetic Radiation," at pp. 1716, Concise Encyclopedia of Science & Technology, McGraw–Hill (1997) 8th Edition, New York, New York.

Parker, Sybil P., (Editor in Chief) "Scattering of Electromagnetic Radiation," at pp. 101–103 Encyclopedia of Science & Technology, McGraw–Hill (1997) 8th Edition, New York, New York.

Considine, Douglas Maxwell, (Editor) "Scattering," at page 2537, Van Nostrand's Scientific Encyclopedia, Van Nostrand Reinhold (1988), New York, New York.

Bohren, Craig F., and Huffman, Donald R., "Physical Basis for Scattering and Absorption," at pp. 3–11; "Absorption and Scattering by a Sphere," at pp. 82–117; "Computation of Scattering Coefficients and Cross Sections," at pp. 126–129; "Gold," at pp. 369–373; and "Homogeeous Sphere," at pp. 477–489, Absorption and Scattering of Light by Small Particles, John Wiley & Sons, Inc. (1983) New York, New York.

Ward–Smith, Stephen, et al.; "Determination of Continuous Particle Size Distributions of Concentrated Sprays," American Laboratory, (Jan. 1999) New York, New York.

Fews, A.P., "Fully Automated Image Analysis of Etched Tracks in CR–39,"at pp. 465–478, Elsevier Science Publishers, (1992) Boston, Mass.

Fleischer, Robert L., "Technological Applications of Ion Tracks in Insulators," at pp. 35–41, Materials Research Society Bulletin, (Dec. 1995) Pittsburgh, PA.

Fleischer, Robert L., "Ion Tracks in solids: From Science to Technology to Diverse Applications," at pp. 17–19, Materials Research Society Bulletin. (Dec. 1995) Pittshburgh, PA.

Federal Register, vol. 58, No. 238, Rules and Regulations, at pp. 65489–65490, (Dec. 14, 1993) Section 835.208, Limits for members of the public entering a controlled area.

Bodman Industries, Internet screen shots, "High Sensitivity Evaporative Light Scattering Detector," 7 pages, P.O. Box 2421, Aston, PA 19014 http://www.bodman.com/html.

Condon, E.U. and Odishaw, Hugh, (Editors) "Light Scattering," at pp. 6–122/6–127, Handbook of Physics, (1958) McGraw–Hill Book Company, Inc., New York, New York.

NE–Technology Ltd., Internet screen shots, "Autoscan 60 System," 12 pages, Bath Road, Beenham, Reading, Berkshire RG7 5PR, United Kingdom http://www.netechnology.co.uk/home.html.

Tasl, HH Wills Physics Laboratory, Internet screen shots, The Radosure RAdon Detctor, Tastrak, 3 pages, Tyndall Avenue, Bristol BS8 1TL, United Kingdom, http://www.physics.bristol.ac.uk/research/TASL/home.html.

Intercast Europe CR–39, Internet screen shots," Applications of CR–39," 4 pages, Bologna, Italy http://boal06.bo.infn.it/intercast/Appli.html.

Wyatt Technology Corporation, Advertisement from American Laboratory, "Light Scattering for the Masses," 1 page., 30 South La Patera Lane, B–7, Santa Barbara, CA 93117 http://wyatt.com.

Leco Corporation, Advertisement from American Laboratory, "lecotrac Particle Size Analyzers," 1 page, 3000 Lakeview Avenue, St. Joseph, MI 49085–2396. http://www.leco.com.

Coulter Particle Characterization, Advertisement from American laboratory, "Coulter Particle Size Analyzer," Beckman Coulter, Inc., 4300 N. Harbor Boulevard, Fullerton, CA 92834–3100, http://www.coulter.com.

"Annalen Der Physik,:" 10 pages, Greifswal, Physikalisches Institut. (Jan. 7, 1908) "Discloses what we see (scattering) from Air" No translation available.

* cited by examiner

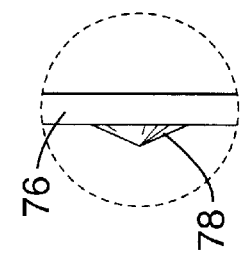
FIG. - 8
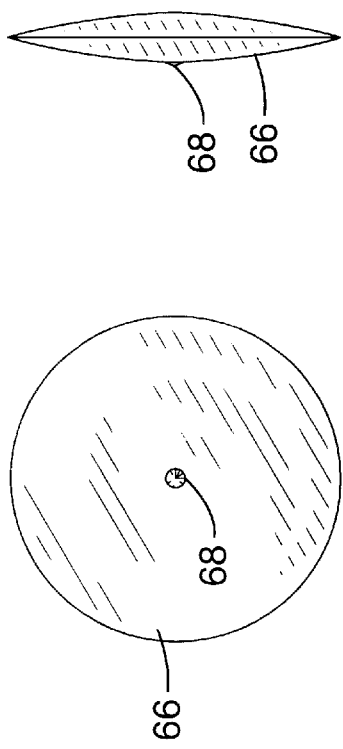
FIG. - 5
FIG. - 4
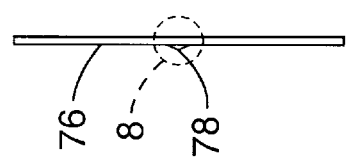
FIG. - 7
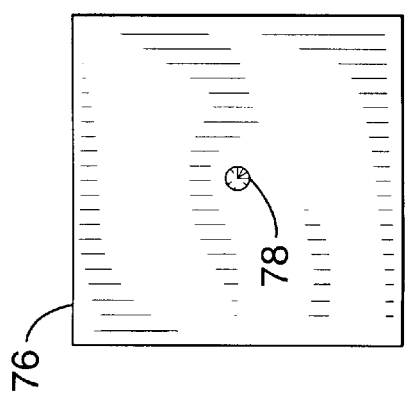
FIG. - 6

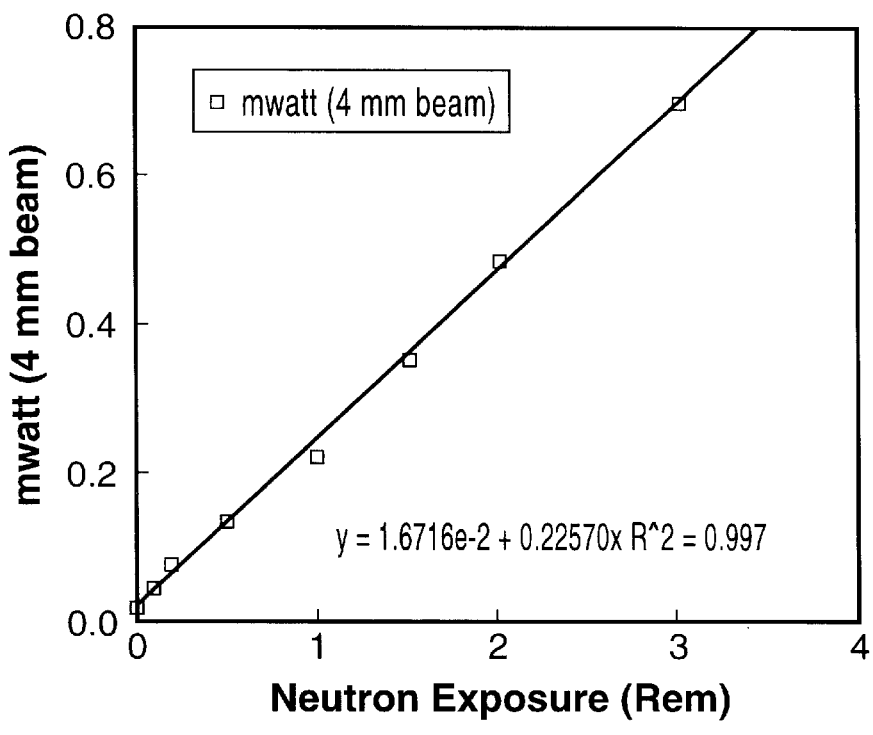
FIG. — 18
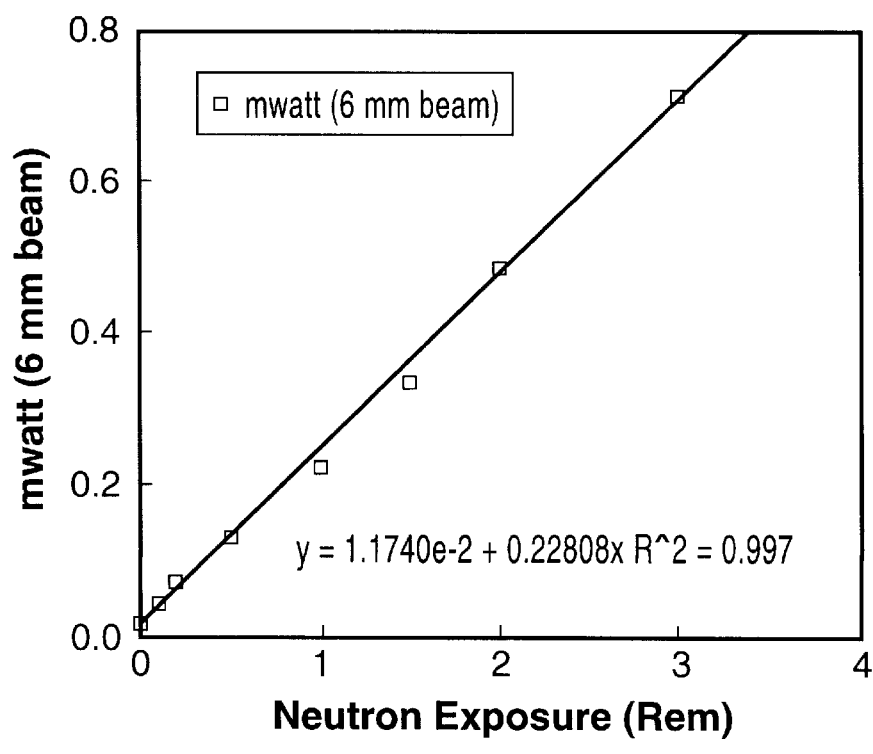
FIG. — 19

LIGHT SCATTERING APPARATUS AND METHOD FOR DETERMINING RADIATION EXPOSURE TO PLASTIC DETECTORS

STATEMENT REGARDING FEDERALLY SPONSORED RESEARCH OR DEVELOPMENT

This invention was made with Government support under contract No. W-7405-ENG-36 awarded by the Department of Energy. The Government has certain rights in this invention.

CROSS-REFERENCE TO RELATED APPLICATIONS

Not Applicable

REFERENCE TO A MICROFICHE APPENDIX

Not Applicable

BACKGROUND OF THE INVENTION

1. Field of the Invention

This invention pertains generally to radiation dosimeters, and more specifically to a device for performing optical analysis of track etch foils used within dosimeters for measuring the extent of cumulative radiation exposure.

2. Description of the Background Art

Dosimeters incorporating track etch foils as a recordation medium are commonly used for assessing cumulative radiation exposure. The most commonly used dosimeter, the thermoluminescent detector (TLD), is used to assess several forms of radiation. In addition to the TLD, the PN-3 track etch dosimeter is used to determine the legal dose-of-record from neutron radiation. The PN-3 dosimeters and standardized dosimeters contain three pieces of CR-39™ clear plastic track etch foils which are 1.5 mm thick by 2 cm wide by 2.4 cm in height. Although sensitive to several types of radiation, these track etch foil dosimeters are more generally used for either radon or neutron dosimetry.

Neutron interaction with the plastic within a dosimeter creates material degradation by the action of recoil protons. After the plastic has been etched in a bath of caustic water (6.00 to 6.25 N NaOH) for a specified length of time (usually several hours), the degradation appears as pits (typically of a conical shape) which are of a diameter from two to thirty microns, and barely visible to the naked eye. As a comparison, the diameter of a human hair is typically about ninety microns. The number of pits on the track etch foil per unit area is directly proportional to the radiation exposure, and when compared with the results from foils exposed to a standard amount of radiation, can be used to calculate the cumulative radiation dose received. Currently, the etched pits are counted manually by visual inspection, or by using a photo-optical inspection station which automatically counts the pits.

Visual inspection, using a microscope of sufficient power, enables the user to count the number of pits within a standard field of view. This method produces acceptable results yet is extremely labor intensive—especially at the high end of exposures (above 2 rem). This method is currently used only as a last resort; yet until the advent of this invention it was the only acceptable method for analyzing the PN-3 foils for high levels of neutron exposure.

Photo-optical inspection for low levels of radiation exposure can be performed on commercial instruments which optically count each pit within the track etch foil after it has been etched. One such instrument, the "Autoscan 60" (NE Technology, Ltd., Berkshire, England), uses magnification and side-lit illumination from a strong light source to make the pits appear as bright areas against a dark background. A video camera images the surface pits within a unit area, and imaging software then counts the number of pits within that area. This instrument is capable of running a carousel of track etch foils, and producing a report. As described in the published information for the Autoscan system, the upper limit for the basic reading of exposure is up to 2 rems (2000 mrem, or 20 mSv). With the use of "extraordinary analysis", it is claimed that the instrument can read exposures up to 10 rem (10000 mrem, 100 mSv). In practice, the instrument shows a linear range which approaches 1.5 rem (1500 mrem, 15 mSv). It will be recognized that accuracy decreases rapidly at high exposure levels because the pits begin to overlap one another with increasing frequency and the visual pit counting process is not generally unable to discern these overlapping pits. The overlapping of the pits within these high exposure samples may account for the "foldback" phenomenon experienced when using the Autoscan system.

The drawbacks inherent in these methods of analyzing radiation exposure levels make it difficult to effectively administer proper safety programs. This is especially true in light of recent government requirements to read accumulated radiation levels up to a five rem exposure.

Accordingly, a need exists for an apparatus and method capable of quickly and accurately measuring accumulated radiation exposure as recorded on standard track etch foil patterns up to at least a five rem level of exposure. The present invention satisfies those needs, as well as others, and overcomes the deficiencies of previous solutions.

BRIEF SUMMARY OF THE INVENTION

The present invention is an optical system that addresses the need for accurately reading dosimeter track etch foils to determine cumulative exposure to radiation. The optical system tests the dosimeter track etch foils by passing a collimated light beam through the sample and measuring the exiting scattered light which is largely a function of the density, and size, of the pits in the surface of the foil. Light scattering was observed and mathematically quantified in 1871 by J.W. Strutt (Lord Rayleigh), and is commonly referred to as Rayleigh scattering. Particles registered by Rayleigh scattering are those which are typically smaller than the wavelength of the scattered light. Equations developed by Gustav Mie describe light scattering for particles of a size comparable to the wavelength of the light. Mie scattering is utilized within the present invention for quantifying voids (pits) within the material of the track etch foils. Additional details of the Mie theory can be found in a variety of physics reference textbooks, including in a reference by C. F. Bohren, entitled "Absorption and Scattering of Light by Small Particles", ISBN 0-471-05772-X 1983, chapter 4, page 82, and in a reference entitled "Encyclopedia of Science and Technology", ISBN 0-07-911504-7,1997 page 70 in a section on "Light Scattering Photometry". Both of these publications are incorporated herein by reference.

The present invention is capable of processing dosimeter track etch foils more rapidly and with greater accuracy than presently available automated commercial instruments, while it extends the range of effective dosimeter analysis to include radiation doses up to five rems (5000 mrem, 50 mSv). The invention determines the relative number and size of etched pits by measuring the amount of light which scatters when a collimated beam is passed through a track etch foil. The light is scattered by the pits on the surface of the track etch foil which are indicative of radiation exposure.

By way of example, and not of limitation, in accordance with the present invention after the track etch foils have been chemically etched by conventional means, they are placed in the path of an intense collimated light source, such as a beam from a helium-neon laser (He—Ne at a wavelength of 632.8 nm), whereby the light is scattered by the pits in the material. The scattered light is collected by a lens, modified by an unscattered light mask, and focused onto a detector or means of registering the intensity of the scattered light. The unscattered light mask blocks the incident beam as it exits from the sample so that the amount of scattered light may be accurately measured, without contributions from the unscattered light. The amount of light scattering which occurs is proportional to pit density and size at the area of beam impingement on the surface of the track etch foil which allows cumulative exposure to be calculated.

Measurements for an unexposed, but chemically etched foil, provide a reference against which scattered light measurements are compared. Unexposed etched reference foils were found to generate negligible amounts of light scatter; only slightly above that which is generated when the track foil sample is removed from the holder to let the light pass through unhindered. When measuring all light exiting an exposed track etch foil, the background light power was found to typically register approximately five times higher than the scattered light when tested at the highest exposure level of five rems. The variation in light intensity received by the detector as a result of light scattering was, thereby, a minor percentage of the overall light power being detected which complicated the calculations of pit density. Masking out the unscattered light allows all remaining light (scattered light) to be registered as indicative of pit density. The unscattered light mask utilized in the present invention is capable of increasing response linearity such that a light intensity of near "zero" will approximate an accumulated radiation level near "zero" rems since the meter is restricted to detecting only the light scattering in response to the pits within the chemically etched foils. The invention therefore provides a number of benefits which aid the analysis of track etch foils used in dosimeters.

An object of the invention is to improve safety for workers involved with radioactive materials by simplifying testing for cumulative exposure to radiation sources, so that more frequent testing may be performed.

Another object of the invention is to provide an apparatus and method for the rapid measurement of accumulated radiation as registered on track etch foils which typically are used within dosimeters.

Another object of the invention is to provide a method that yields accumulated radiation measurements that are highly accurate.

Another object of the invention is to provide a method capable of measuring high levels of accumulated radiation up to and including at least five rems.

Another object of the invention is to provide a method capable of taking light scatter angles into account to further enhance accuracy of the measured exposure level.

Another object of the invention is to provide a measurement apparatus that may be constructed from generally available materials and devices.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 4 is a front view of the lens shown in FIG. 3.

FIG. 5 is a side view of the lens shown in FIG. 4.

FIG. 6 is a front view of the detector filter shown FIG. 3.

FIG. 7 is a side view of the detector filter shown in FIG. 6.

FIG. 8 is a detailed side view of the unscattered light mask shown in FIG. 7.

FIG. 18 is a graph of dosimeter measurement linearity over a linear range for a 4 mm light beam.

FIG. 19 is a graph of dosimeter measurement linearity over a linear range for a 6 mm light beam.

DETAILED DESCRIPTION OF THE INVENTION

Referring more specifically to the drawings for illustrative purposes, the present invention is embodied in the light scattering apparatus generally shown therein and the associated method for determination radiation exposure. It will be appreciated that the apparatus may vary as to configuration and as to details of the parts, and that the method may vary as to the specific steps and sequence without departing from the basic concepts as disclosed herein.

Figure 1:
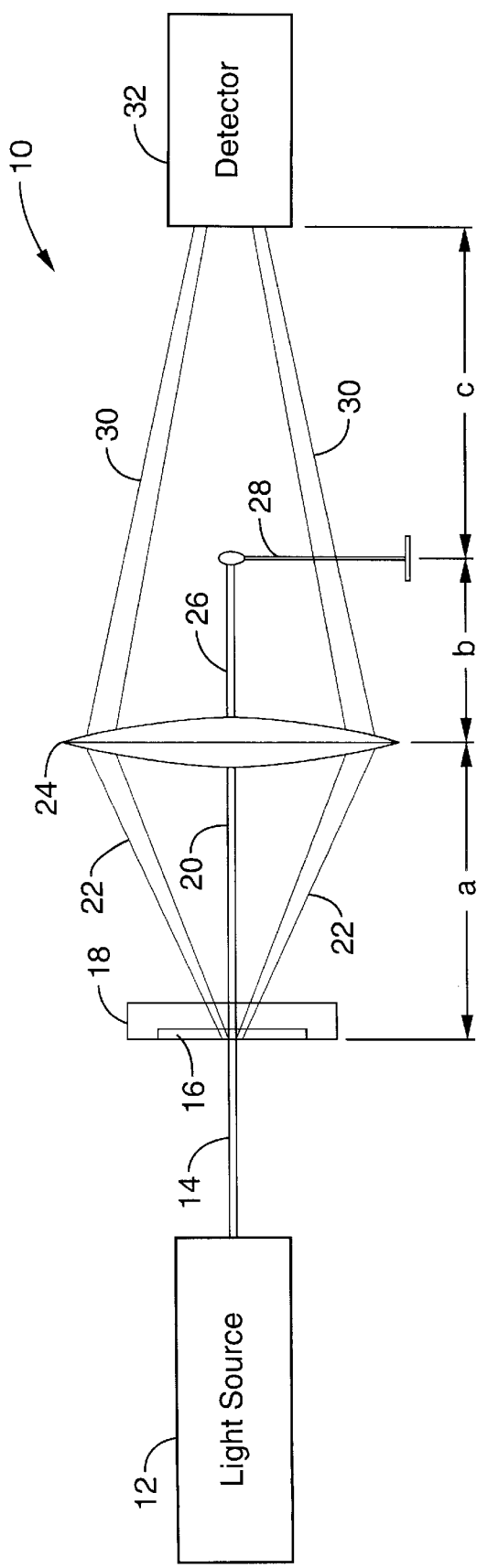
FIG. 1 is a schematic diagram of an optical test system embodiment according to the present invention shown scattering collimated light as it passes through a track etch foil which has been exposed to radiation.

FIG. 1 shows an apparatus 10 for determining cumulative radiation exposure as registered by plastic track etch foil type detectors (dosimeters) according to the invention. Light is generated by a collimated high-intensity light source 12, such as a He—Ne laser, that is preferably adjusted for optical alignment using a standard optical mount (not shown). Light from the He—Ne laser, at a 632.8 nm wavelength, is used within the embodiment due to its high intensity and ease with which the beam may be to collimated and focused. However, any collimated high-intensity light source may be correctly used within the invention, such as a collimated white light source, or laser diodes which should be of particular utility.

Figure 2:
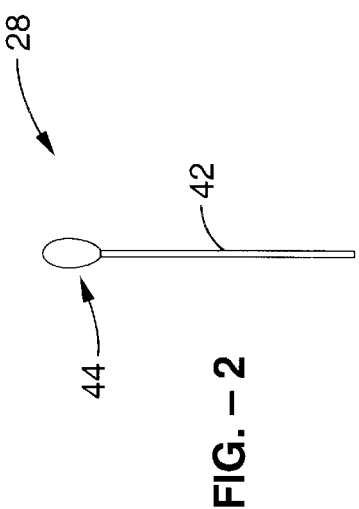
FIG. 2 is an elevation view of the unscattered light mask of FIG. 1.

The light source 12 emits a collimated light beam 14 which strikes track etch foil 16 retained by holder 18. The track etch foil is retained over a beam aperture (i.e. an 8 mm circular aperture) within the holder that allows the light to pass through. Preferably, the holder 18 is attached to an optical mount (not shown) to allow for precise positioning of the sample. Track etch foils with known exposure levels were created for testing by exposing blank dosimeter track etch foils to known amounts of neutrons from a $^{252}$Cf source so that test results could be easily correlated with a known value. Included within the set of samples were a "blank" sample which had not been exposed to radiation, but had been identically etched. A range of exposure levels were tested within the inventive apparatus, wherein the samples collectively received cumulative exposures spanning from 0.0 rem to 5.0 rem (0.0 mrem to 5000 rem, or 0 mSv to 50 mSv). To provide direct comparison testing, the identical samples tested by the present invention were subsequently analyzed by a qualified technician using a commercially available instrument (e.g., an Autoscan 60). In setting up the inventive apparatus, the track etch foil 16, and the holder 18, are aligned substantially perpendicular to the light beam 14, such that the beam passes generally through the center of the aperture with the attached track etch foil. Exiting the rear of the track etch foil 16 is the unscattered light beam 20 and rays of scattered light 22 induced by the pits within the track etch foil 16. The scattered light 22 is collected by a lens 24. The lens 24 is exemplified as a 3.5 cm diameter lens with a 10 cm focal length which is mounted along the optical path of the non-scattered beam. Referring also to FIG. 2, the unscattered light mask 28 is exemplified as a thin wire 42 that is configured on one end for mounting and on the opposite end with a circular mask 44. The mask should be of a sufficient diameter to block the "straight-through" (unscattered) beam and overcome minor alignment errors. The mask is preferably non-reflective to prevent unscattered light from being reflected into the detector and registered as scattered light. Black paint may be used to provide a non-reflective surface for the mask. The mask used herein was formed from a single piece of malleable wire 42, with the mask 44 being formed by pressing it to a diameter of approximately one millimeter for use with a beam diameter slightly less than one millimeter. The mask 44 blocks the beam of unscattered light 26 as it exits the collection lens 24. The wire 42 with the attached mask 44 are connected to an adjustable mount which is placed in the optical path of the focused beam of unscattered light. The scattered light 22 from the track etch foil 16, which was collected by lens 24 is focused as a converging beam 30 onto light detector 32. Light detector 32 measures the optical power of the scattered light which corresponds to pit density and size in the portion of the track etch foil upon which the incident beam impinges. The lines 22 and 30 in FIG. 1 represent three dimensional cones of scattered light (not individual light beams). An optical power meter may be used as a simple light detector to register the scattered light focused by lens 24. It will be appreciated that the unscattered light is not registered by the optical power meter and that the scattered light being detected is thereby substantially proportional to the cumulative radiation exposure. As a consequence, a straightforward readout or display can be provided by calibrating the scale of the power meter to readout the cumulative radiation exposure, i.e. in rems. Approximate distances within the optical system of FIG. 1 are: a at 11.0 cm, b at 8.5 cm, and c at 15.0 cm. The distances are adjusted to achieve maximum response from a foil exposed to 5 rems and a minimum response from the unexposed "blank" sample. The distances between the optical elements are provided by way of example and are dependent upon the type and collimation of the entrance beam and the size and type of lens used for focusing the scattered light.

Figure 3:
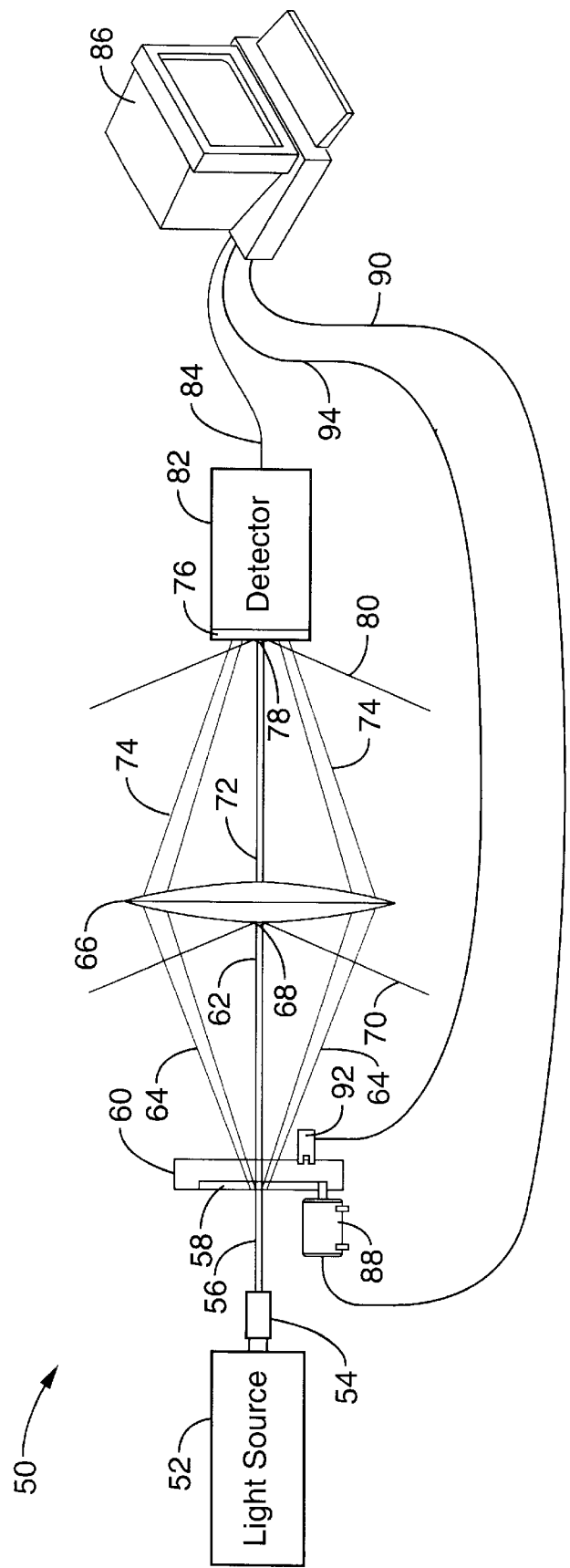
FIG. 3 is a schematic diagram of an optical test system embodiment according to the present invention shown utilizing a laser light source and a computer for data collection.

In FIG. 3 another embodiment 50 of the light scattering apparatus is shown. A laser light source 52 has a telescopic lens 54 that allows the size of beam 56 to be adjusted while maintaining collimation. In the exemplified embodiment, the telescope lens 54 preferably allows adjustment of the collimated light beam 56 from approximately one millimeter to ten millimeters in diameter. The use of a wider beam diameter provides a resultant scattering pattern with contributions from a larger number of pits which can provide an error-reducing averaging mechanism for the measured scattering response. The light beam, preferably a laser light source, is incident on the track etch foil 58 held in a holder 60. Exiting rearward of the track etch foil 58, are the primary beam 62 which corresponds to the incident beam 56, along with diffuse radiating scattered light 64 which has been scattered by the holes and pits within the foil. A lens 66 collects the light, which has been scattered as a three-dimensional cone of light, and focuses it onto a light detector 82.

The embodiment in FIG. 3 is shown with a different unscattered light mask than illustrated in FIG. 1. It will be recognized that a light mask to block the unscattered light, may be placed at any location along the path of unscattered light between the track etch foil sample and the light detector. Two unscattered light masks are exemplified in FIG. 3, with a first mask 68 located centrally on the lens 66 and preferably having a flattened cone-shaped reflective structure. FIG. 4 and FIG. 5 show the lens 66 with cone-shaped mask 68 in detail. Referring again to FIG. 3, the scattered light 64 is focused by the lens 66, which emerges as scattered light 74 focused on a filter 76 to which is mounted a second unscattered light mask 78 which is proximal to the aperture of a photo-detector 82. Use of multiple light masks can facilitate the process of beam alignment for the system. FIG. 6 and FIG. 7 show the filter 76 having an attached unscattered light mask 78, while FIG. 8 provides a detailed side view of the light mask 78. It should be recognized that embodiments of the unscattered light mask are provided as illustrative examples of the numerous methods in which the unscattered light may be prevented from being registered by the optical detector.

The photo-detector 82 of FIG. 3 generates serial output data which is received by an electronic system for displaying and/or performing computations on the data. A computer system 86 operatively connected via cable 84 exemplifies a computation and display system. Alternatively, an analog output from a photodetector module could be input to a meter readout, or to an A/D (analog-to-digital) converter on a data-acquisition board which is under computer control. The computer 86 is preferably used to perform calculations and record data from each track etch foil within a group of dosimeter samples. The computer may be running a fully custom program for controlling the dosimeter testing system or be executing instrument control programs such as Lab- View™ which is manufactured by National Instruments Corporation of Austin Tex. The software provides a means of calculation and recordation of the test data in addition to control and synchronization of system elements.

FIG. 3 additionally illustrates an optional geared motor 88 which is connected via cable 90 to allow for control by the computer 86 of sample position. The motor 88 is preferably configured to engage a rotatable holder for the track etch foil sample 60. The beam passing through the track etch foil has been set off-center of the axis of rotation, such that during rotation, the incident light subscribes a circle on the track etch foil wherein the scatter contribution from pits within that area are averaged by the photo-detector 82 and the measurements taken during the rotation (spinning) of the sample are further averaged by the computer. Alternately, the photodetector could be set for a long-enough capture (exposure) interval to perform all averaging within a single sample. Averaging the measurements over a larger area of the track etch foil improves the accuracy of the measurements. Alternative methods of changing the optical path on the track etch foil can be employed to provide repetitive translation movements. Specifically, the above rotational drive unit can employ another gear set driven by the rotating motor drive which provides a spiral-path illumination of the track etch foil test sample whereby an average is taken over a larger area. The foil sample may alternatively be driven by a stage in a programmed sequence of X and Y movements, or similar translations.

Furthermore, a barcode may be encoded, or attached, on each track etch foil to provide information such as dosimeter ID, or employee number. An arc-shaped barcode may be encoded on the samples within this embodiment and aligned such that the rotation of the sample by the motor also moves the bar code over a bar code reader 92, thereby alleviating the need of moving the bar code reader. The bar code reader 92 is shown connected via cable 94 to the computer so that dosimeter information and test data may be simultaneously registered for each dosimeter sample tested. Various forms of dosimeter sample translations, such as linear, box-shaped, and line-scanned may be utilized with similar results, and the bar code reader can likewise accommodate these translation variations. Sample number encoding on an "Autoscan 60" utilizes a proprietary "dot" based system for encoding the sample number.

Figure 9:
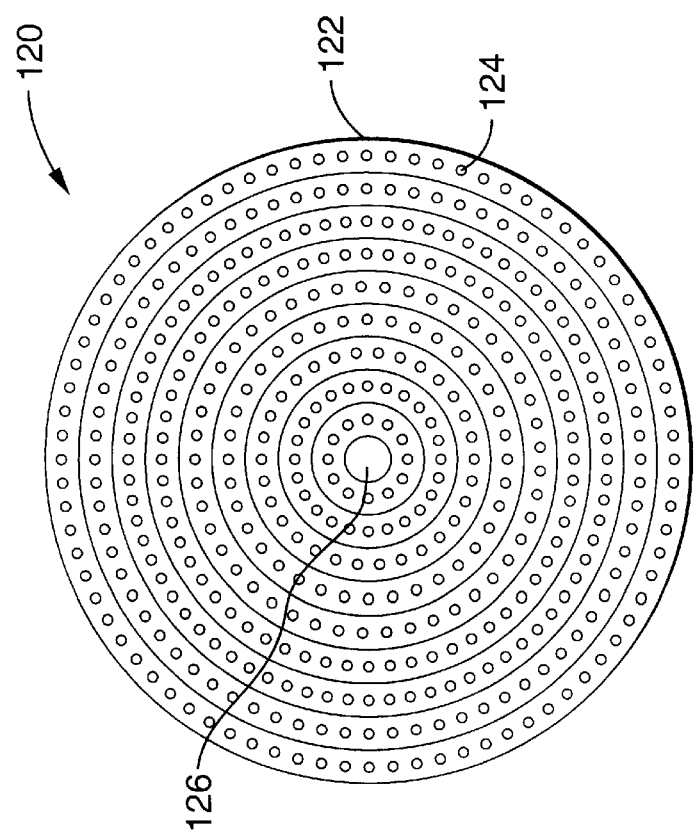
FIG. 9 is a front view of a representative ring-structured optical detector array according to an embodiment of the present invention.

FIG. 9 shows a ring-structured photo-detector 120 that can be employed as the optical power detector within the invention. The photo-detector 120, comprises a circular array 122 of photo-sensitive elements 124; such as photo-transistors, photo-diodes, or similar photo-sensitive elements which are arranged around a central "bulls-eye" section 126. The area of the "bulls-eye" captures the beam of unscattered light so that its power level is not registered, therefore, the "bulls-eye" section preferably does not contain any optical elements. The "bulls-eye" may be configured with an aperture to allow the unscattered beam to pass through so that reflections from a surface of the "bulls-eye" are not allowed to adversely effect the accuracy of the readings. As an alternative to a "bulls-eye", a radially arranged optical detector can be configured to allow electronic "muting" of any desired diameter circle about its center (i.e. a "bulls-eye" with a configurable size). Preferably the "bulls-eye" optical detector is configured so that light intensity as received by each ring is separately summed so that angular displacement may be factored into the scatter calculation. The Raleigh and Mie equations are then used to correlate scattering angle with pit size which is related to the energy distribution of the radiation exposure which created the pits within the track foil. A set of weighting values are calculated for the particular implementation of the system within each ring of the optical detector array. The weighting values are based on Raleigh and Mie calculations. To create the weighting values, a scatter angle is calculated from the inverse tangent of the radial distance over the virtual distance from point of scatter to the optical detector. The virtual distance is a calculated or empirically derived value that takes into account the lens optics. The scatter angle then is correlated with pit size from which is found a weighting factor for that particular radial distance. (Refer to the references cited on Mie scattering for in depth discussion of scattering angle.) The weighting values then can be directly applied to each radial ring by multiplying the intensity value of the ring by the weighting factor. A weighted sum of the optical energy which corresponds with the scattering of the light is the result. These weighting factors may also be designed into the ring hardware such that a single output is provided by the optical detector as a weighted radial sum of the optical power received. The cumulative radiation exposure in rems may then be calculated from this weighted sum. A weighted sum should provide increased accuracy over a non-weighted optical power value. It will be appreciated that a simple form of weighted sum may be obtained from the optical detector of FIG. 1 by configuring the aperture of the detector with a graduated annular filter whose transmissivity decreases toward it center. The intensity of the light which has been scattered through a narrow angle is attenuated upon entering the detector while the light scattered through large angles is passed into the detector with less attenuation. The optimum graduation profile may be calculated in the same manner as the weighting for the aforesaid optical detector rings.

Figure 10:
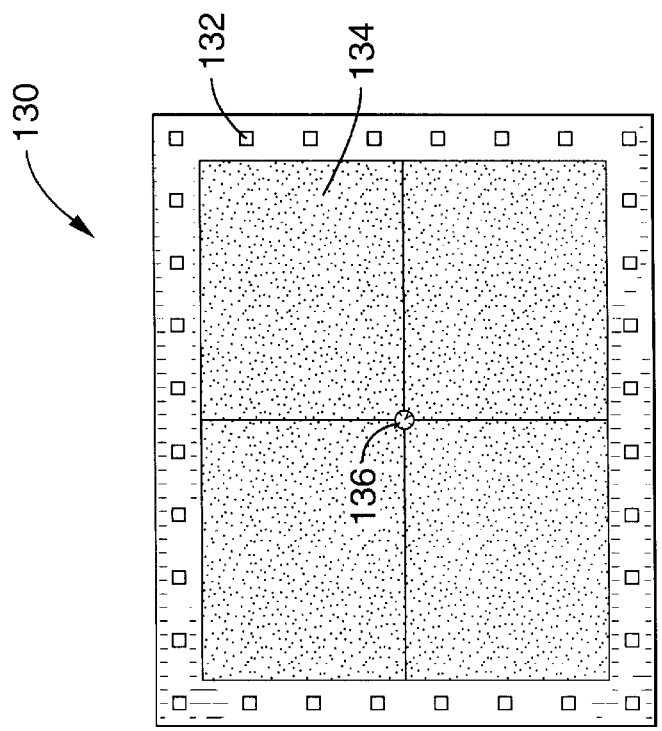
FIG. 10 is a front view of a representative CCD array configured as an optical detector array according to an embodiment of the present invention.

FIG. 10 shows a Cartesian-structured optical detector 130 exemplified as a charge-coupled device (CCD) imaging array. A variety of CCD arrays are available with sizes presently approaching $^{3/4}$ of an inch square. A typical bare CCD die has electrical connection pads 132, and an optical surface 134 comprising cells generally divided into four quadrants. In accordance with an embodiment of the present invention, a standard monochrome CCD imager is fitted with an unscattered light mask 136 which blocks the beam of unscattered light to prevent it from being registered on the image cells of the CCD. To arrive at an overall intensity value from which scattered light may be calculated using this CCD imager, the intensities of each pixel are summed. Note that in the embodiment of FIG. 1, this overall sum of intensity was performed automatically by the optical detector which was an optical power meter, and no additional calculations were required. Employing a CCD imager in the embodiment of FIG. 1 would generally require a computational element to calculate the sums. Numerous calculations are required when using a CCD for a detector, however, additional benefits can be gained by the ability to perform additional field calculations, although the serial nature of the calculations naturally increase the time required to analyze a track etch foil. If the scatter angle of the light is to be taken into account to calculate the accumulated radiation exposure in rems then calculations must be performed on each pixel within the view field of the CCD, because the radial distance of each pixel in the field must be calculated, weighted, and summed. The computer can perform a series of these calculations which may be averaged over any interval, such as corresponding to a fixed number of translational movement cycles of the track etch foil. Employing the CCD imager does allow an image of scattered light intensity to be displayed on the monitor of the computer or on a separate monitor to provide visual feedback. Additionally, the computational power of the computer may be used for other related image calculations within the environment.

Figure 11:
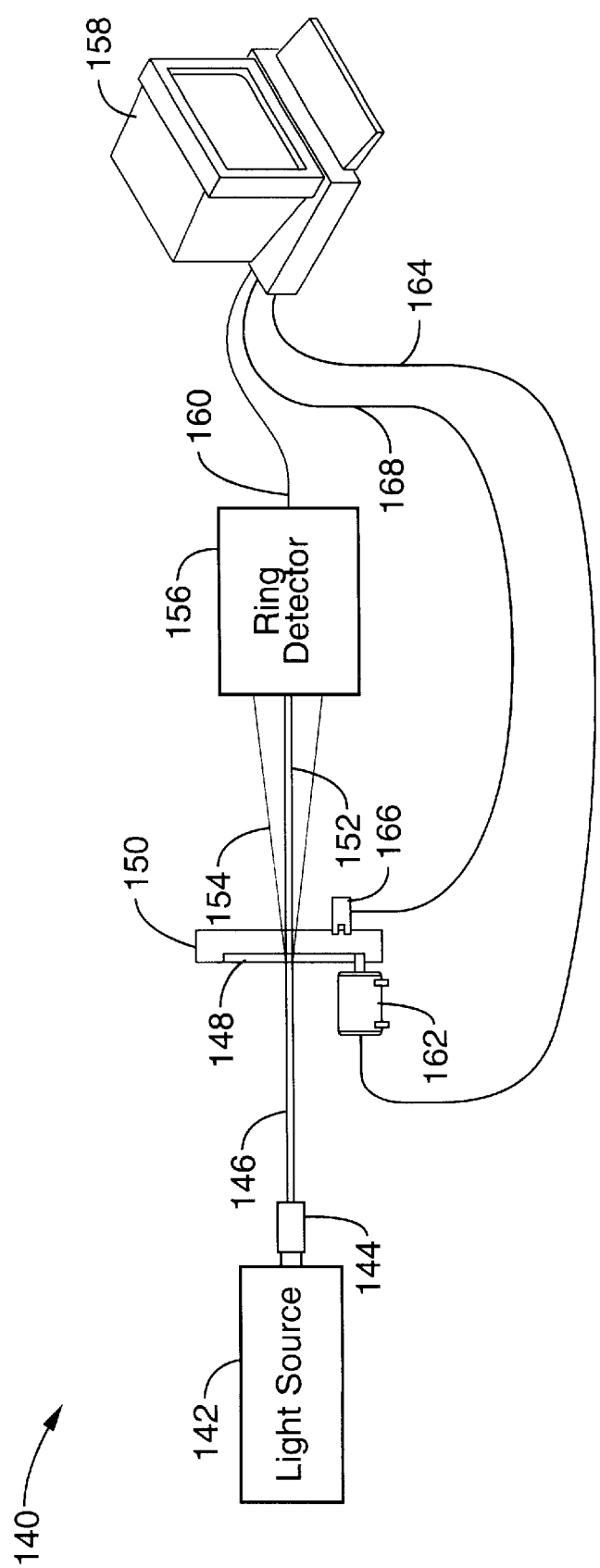
FIG. 11 is a schematic diagram of an embodiment of the optical test system according to the present invention shown utilizing the ring-structured optical detector of FIG. 9.

FIG. 11 shows an embodiment 140 of a light scattering apparatus which determines the radiation exposure of plastic detectors using the ring structured photo-detector shown in FIG. 9, or alternately the CCD imager shown in FIG. 10. A collimated light source 142 employs a telescope lens arrangement 144 to generate an adjustable diameter beam 146 set to impinge upon a track etch foil test sample 148 in a holder 150. The scattered light 154 which results from the incident beam striking the pits and holes within the foil is not collected by a lens in this embodiment; instead, it is registered directly by the ring structured optical detector 156. The unscattered light of the beam 152 emerging from the track etch foil is aligned with the non-responsive "bulls-eye" portion of the optical-detector and is thereby masked; so as not to be summed with the scattered light being registered by the detector.

Unlike previous methods of detecting pits in track etch foils, the method of the present invention does not rely on the tedious sequential process of counting each pit individually. Additionally, the scatter calculations take into account overlapping pits so that accuracy is improved. The parallel nature of the optical scattering method of the present invention allows a measurement to be performed almost instantaneously once the apparatus is properly loaded with the track etch toil. Therefore, the speed of an automatic test unit based on this form of parallel test apparatus is determined largely by the speed at which the sample can be placed within the system. It is estimated that sequential loading of a new sample will take approximately one second within an automated system similar to the carousel devices currently in use within the Autoscan system.

EXAMPLE 1

A commercially available automatic reader was used to correlate the measurements which were taken by the apparatus shown in FIG. 1. The commercial reader used was an "Autoscan 60", manufactured by NE Technology Ltd., and the samples were tested by a qualified technician in two different sampling areas. The resultant data is shown in Table 1 wherein the entries marked "-NE-" (No Estimate) were ones for which no estimate was available from the instrument, and those marked "-NR-" (Not Run) were for measurements not being run. The values given as "~nnnn" were provided as estimates by the machine.

Figure 12:
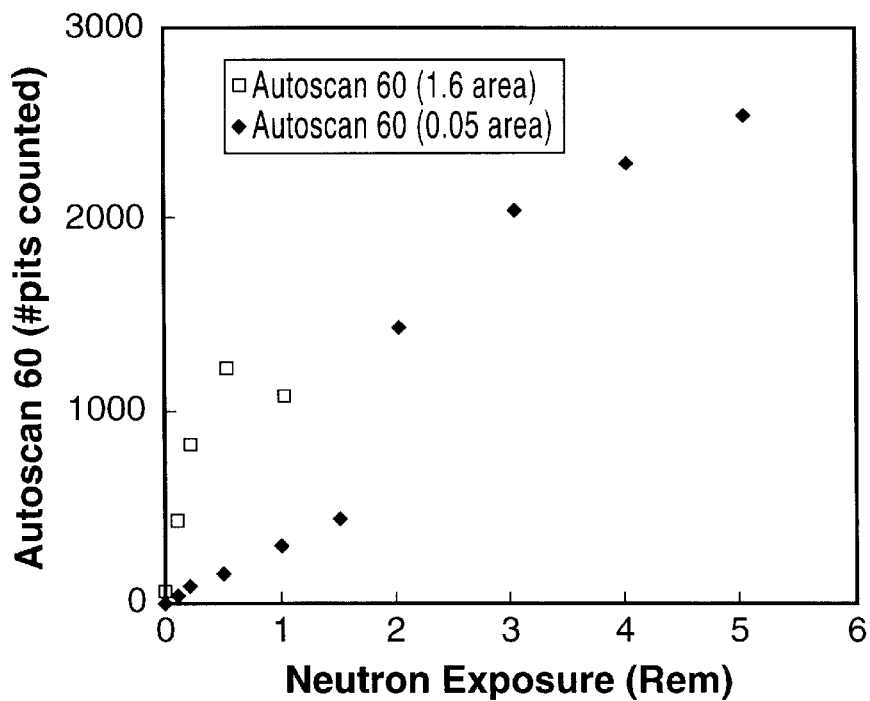
FIG. 12 is a graph of dosimeter measurement linearity on a commercially available system showing results from track etch foil areas of 0.05 mm and 1.6 mm.

The larger 1.6 mm test area listed in Table 1 had a useful linear range of up to 0.2 rem but is shown graphically up to 1.0 rem. FIG. 12 is a graph of these results from the Autoscan device wherein a "foldback" region may be clearly seen. The samples were then tested again using a smaller image area of 0.05 mm, wherein result values were provided up to 5.0 rem (5000 mrem, 50 mSv). Values provided by the "Autoscan 60", within the 2–5 rem range were values which the system "estimated" by use of correction algorithms that take into account the "foldback" phenomenon. The results indicate a linear response for the smaller image size up to and including the 1.5 rem exposure, yet a non-linear response beyond that level.

Figure 13:
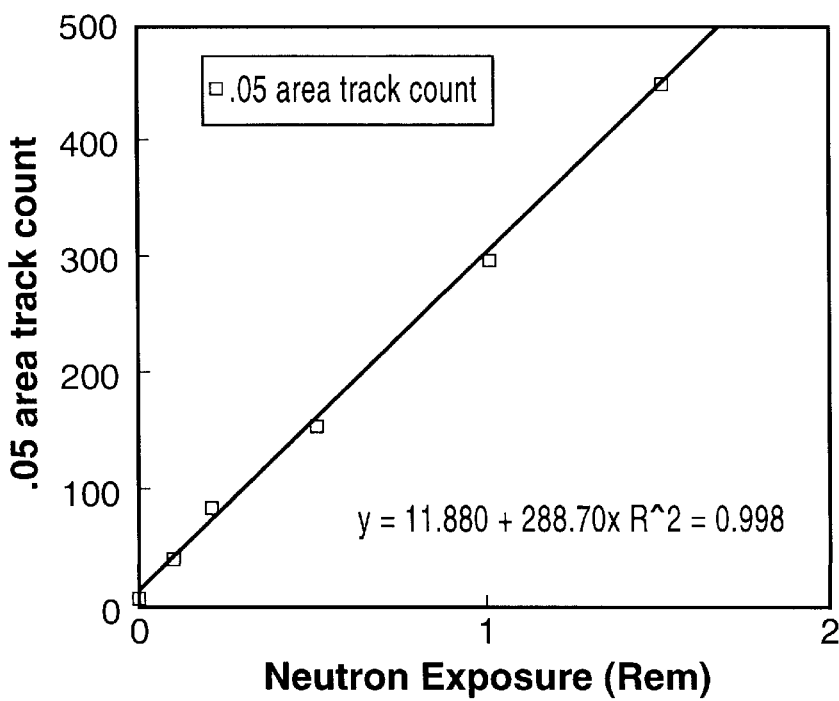
FIG. 13 is an expanded graph of the linear region of the 0.05 mm track etch foil area of FIG. 12.

FIG. 13 shows a calculated linear regression fit of 0.998 (1.000 is a perfect fit to a straight line) on the data from the linear portion of the measurement for the 0.05 mm area.

EXAMPLE 2

The aforesaid samples were also tested using 2, 4, and 6 mm beam diameters in the embodiment of the invention generally described in FIG. 1. The test setup, however, employed the telescoping lens as in FIG. 3. A He—Ne laser with a measured power output of 5.6 milliwatts was utilized as the collimated light source and the resultant test readings of optical power from the optical detector, (a power meter in this case) are listed in Table 2 in milliwatts.

Figure 14:
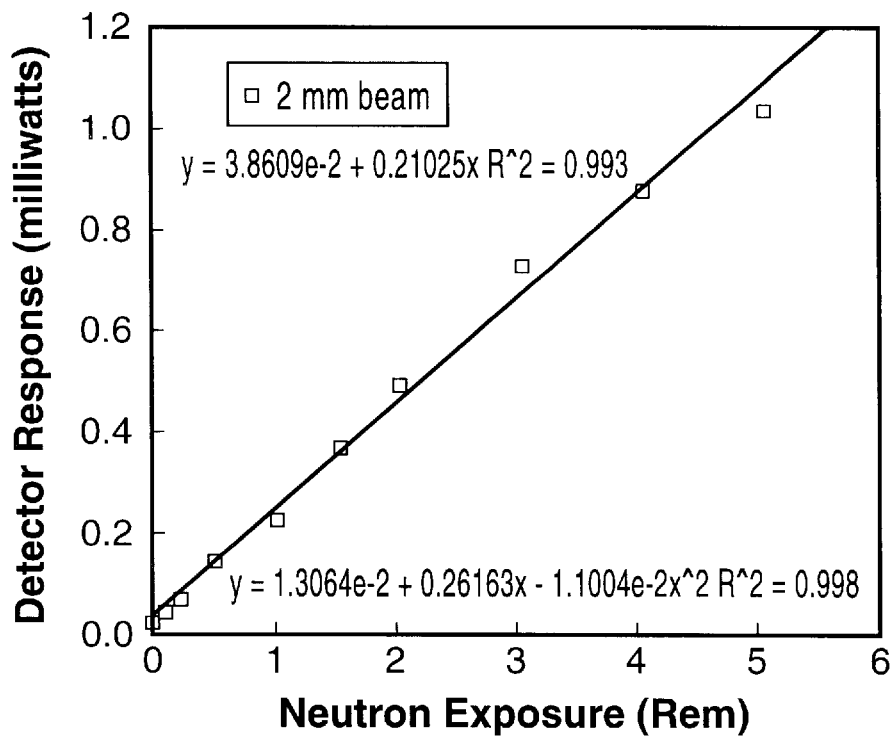
FIG. 14 is a graph of dosimeter measurement linearity for a light beam with a diameter of 2 mm.
Figure 15:
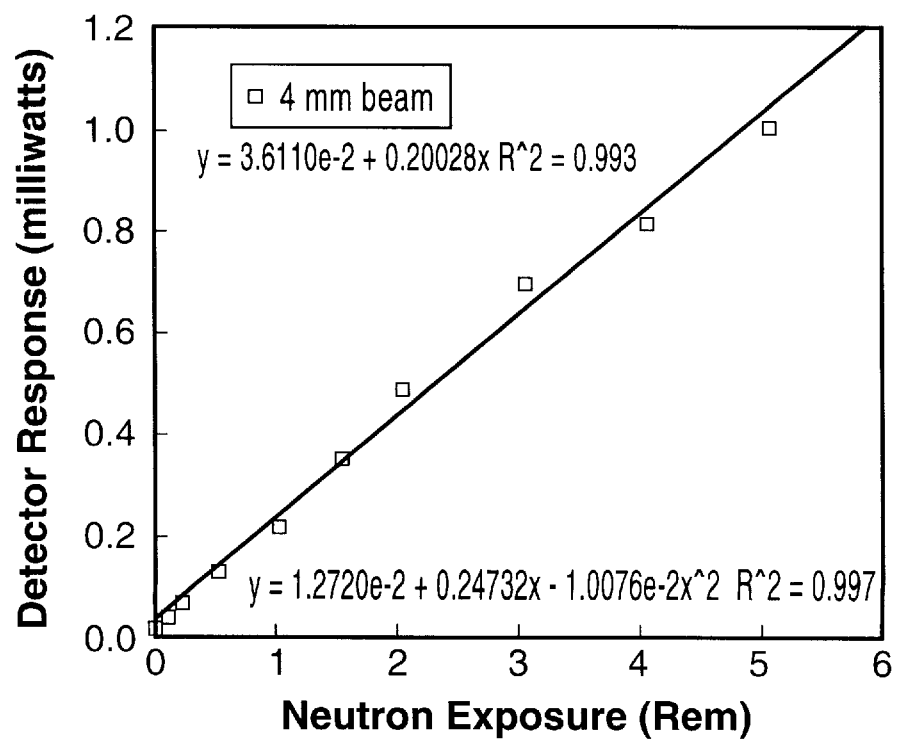
FIG. 15 is a graph of dosimeter measurement linearity for a light beam with a diameter of 4 mm.
Figure 16:
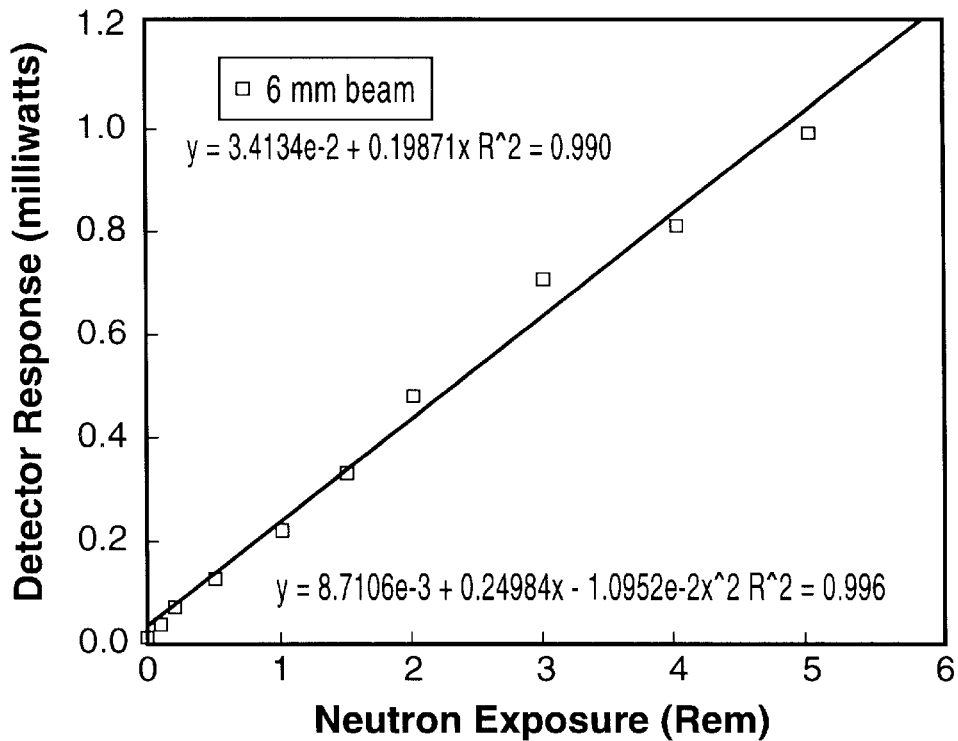
FIG. 16 is a graph of dosimeter measurement linearity for a light beam with a diameter of 6 mm.

The data for the beam scattering tests are graphed separately according to the diameter of the light beam, whereas results for a 2 mm beam diameter are shown in FIG. 14, a 4 mm beam diameter in FIG. 15, and a 6 mm beam diameter in FIG. 16. Correlation calculations are shown on each graph with a linear fit calculation and a second degree polynomial fit calculation provided on select graphs.

The linearity (0.990–0.993) of the test data indicates that the test method provides an accuracy sufficient for general use, while the second degree polynomial fit ("French Curve") provides a more accurate analysis (correlation coefficients of 0.996–0.998) across the full range of exposures (0.10 rem to 5 rem).

Figure 17:
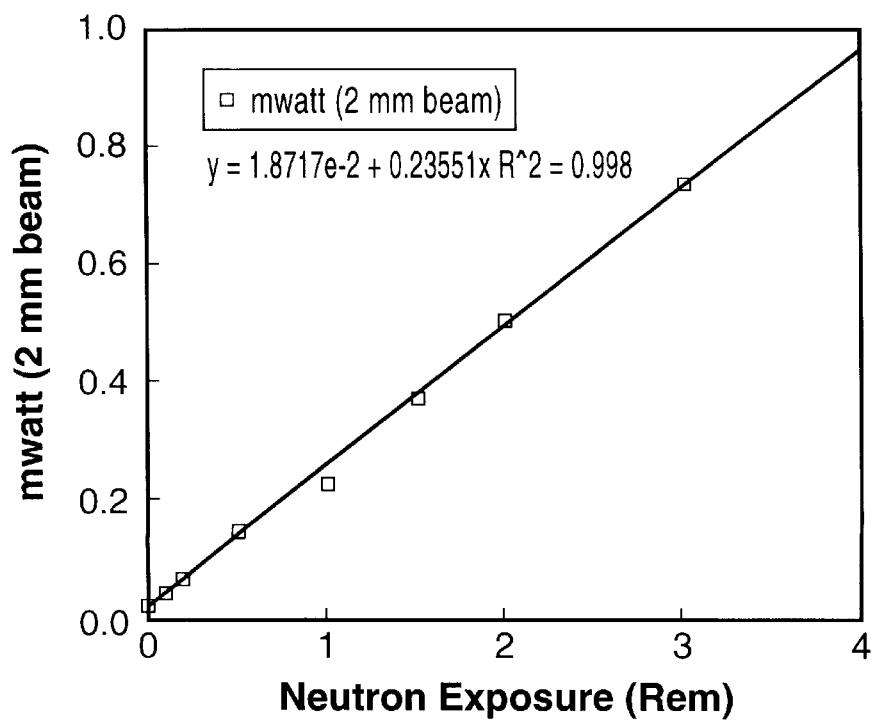
FIG. 17 is a graph of dosimeter measurement linearity over a linear range for a 2 mm light beam.

The linear range of the data for the 2, 4, and 6 mm beam sizes are shown in the graphs of FIG. 17, FIG. 18 and FIG. 19, respectively. This linear range is shown up to the 3 rem exposure level, with correlation coefficients of 0.997–0.998. The intensity of the scattered laser light from the 2 mm beam is slightly higher than that of the 4 mm and 6 mm diameter beams as the focus of the beam is tighter. The smaller 2 mm beam has a higher intensity (watts/cm$^2$), and therefore generates a greater overall intensity of scattered light. Note that this is true, even for the blank (unexposed) dosimeter sample. A wide beam, however, is preferred as it inherently provides averaging of the pit density which may eliminate the necessity of performing additional measurements from different areas on the foil. It is expected that the resolution of the test at the lower end of the radiation exposure range can be improved by employing a light source having a higher power than the 5.6 mW source used for these measurements.

The optical test system of the present invention is exemplified for use in detecting pits within the foils of a radiation dosimeter, however, it should be appreciated that the invention may be utilized for the detection of pits, voids, or small particulates within a variety of generally transparent materials. Experiments were conducted utilizing the inventive apparatus for detecting air bubbles and/or small particulates suspended within a clear material. Test samples of clear resin were produced having embedded air bubbles or glass spheres. A configuration similar to FIG. 1 was employed for the experiment, and the results from a measurement on multiple samples correlated with a manual inspection using a microscope. It should be recognized that the bubbles and particulates were suspended within a hardened clear material, instead of a liquid whose properties are subject to change, so that the results could be correlated between multiple tests with a manual inspection. Therefore, it will be appreciated that the present invention may be employed for the testing of both solids and liquids.

Accordingly, it will be seen that this invention can be used for accurately and quickly analyzing track etch foils from dosimeters, such as the CR-39™ foils used as detectors for radon, and other radiation sources. Embodiments have been shown which are capable of performing semi-automatic testing, and testing may be extended into fully automatic operation, wherein dosimeter track etch foil samples enter and are tested without the need of user intervention. It will also be appreciated that the invention may also be less preferably utilized for testing transparent materials other than dosimeter track etch foils for various particulates, voids, or similarly small anomalies.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element. in the singular is not intended to mean "one and only one" unless explicitly so stated, but rather "one or more". All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

TABLE 1

Autoscan 60 data from Standard CR-39 ™ foils

| Neutron Exposure | Area 1.6 mm | Area 0.05 mm |
|---|---|---|
| Zero | 59 | 6 |
| 0.1 | 427 | 40 |
| 0.2 | 829 | 83 |
| 0.5 | 1218 | 151 |
| 1.0 | 1081 | 296 |
| 1.5 | -NE- | 448 |
| 2.0 | -NE- | ~1436 |
| 3.0 | -NR- | ~2037 |
| 4.0 | -NR- | ~2285 |
| 5.0 | -NR- | ~2553 |

TABLE 2

Laser Scattering data from Standard CR-39 ™ foils (milliwatts)

| Exposure (rem) | 2 mm | 4 mm | 6 mm |
|---|---|---|---|
| Zero | 0.023 | 0.017 | 0.015 |
| 0.1 | 0.046 | 0.042 | 0.040 |
| 0.2 | 0.070 | 0.074 | 0.071 |
| 0.5 | 0.143 | 0.130 | 0.126 |
| 1.0 | 0.226 | 0.217 | 0.220 |
| 1.5 | 0.370 | 0.350 | 0.330 |
| 2.0 | 0.496 | 0.483 | 0.479 |
| 3.0 | 0.730 | 0.694 | 0.706 |
| 4.0 | 0.880 | 0.818 | 0.806 |
| 5.0 | 1.039 | 1.001 | 0.986 |

What is claimed is:

1. An apparatus for analyzing the cumulative radiation to which a dosimeter track etch foil has been exposed, comprising:
    means for illuminating a track etch foil with high intensity collimated light;
    means for registering the optical power of the light which is scattered by pits within the track etch foil as the collimated light beam passes through the track etch foil; and
    means for determining the density of pits on the areas of the track etch foil illuminated by the collimated light, said pit density being proportional to the registered optical power of the scattered light.

2. An apparatus as recited in claim 1, wherein the light scattered by the pits on the track etch foil is converted to a cumulative radiation exposure level, such as one is given in rems.

3. An apparatus as recited in claim 1, wherein the illuminating means comprises a laser light source capable of being directed to impinge upon the track etch foil.

4. An apparatus as recited in claim 1, wherein the optical registration means comprises an optical detector which is capable of providing an electrical output responsive to the intensity of the light it receives.

5. An apparatus as recited in claim 1, wherein the optical registration means further comprises a mask which is capable of blocking unscattered light from being registered by the optical registration means, wherein the unscattered light is that light which passes through the track etch foil without being deflected by the pits therein.

6. An apparatus as recited in claim 1, wherein the pit density determination means comprises an optical power meter responsive to the intensity of the scattered light being received and calibrated to readout the cumulative radiation exposure.

7. An apparatus for analyzing the cumulative radiation exposure of a track etch foil from a dosimeter that contains pits caused by radiation exposure, comprising:
    a high intensity light source capable of generating a collimated beam of light along an optical path which impinges upon a track etch foil; and
    an optical detector positioned along said optical path which is capable of registering the optical power of the light which has been scattered by the pits on the track etch foil, wherein the value registered for the optical power of the scattered light is proportional to the number and size of pits.

8. An apparatus as recited in claim 7, wherein the light scattered by the pits on the track etch foil is converted to a cumulative radiation exposure level, such as one given in rems.

9. An apparatus as recited in claim 7, further comprising a lens positioned along the optical path between the track etch foil and the detector, said lens directing the scattered light to the detector.

10. An apparatus as recited in claim 9, wherein said lens is fabricated from a transparent material, such as glass or plastic, in any form factor, such as conventional, or Fresnel, that is capable of focusing light.

11. An apparatus as recited in claim 7, wherein the detector utilizes an optical mask to intercept the unscattered light, so that only scattered light is registered, the optical mask being positioned between the track etch foil and the optical element of the detector.

12. An apparatus as recited in claim 7, further comprising a holder for retaining said track etch foil along the optical path.

13. An apparatus as recited in claim 12, wherein said holder is configured to allow translational movements of the retained track etch foil when urged by a mechanical power source, wherein the translational movements of said track etch foil result in measurements being take of scattered light which are averaged over an area of the track etch foil that exceed the area of the collimated beam size.

14. An apparatus as recited in claim 13, further comprising a bar code reader proximal to said holder, wherein during movement of the track etch foil within the holder, a bar code indicia on the track etch foil passes across the fixed location of the bar code reader such that the bar code reader registers the data contained on the bar code indicia of the track etch foil.

15. An apparatus as recited in claim 7, wherein said high intensity light source comprises a laser.

16. An apparatus as recited in claim 7, further comprising a telescopic lens positioned along the optical path between the high intensity light source and the track etch foil, wherein the light beam received from the light source enters the telescopic lens as a light beam of a first diameter and exits the telescopic lens as a light beam of a second diameter.

17. An apparatus as recited in claim 7, wherein said optical detector outputs an electronic output signal in response to the optical power of the scattered light which is being received by the optical detector.

18. An apparatus for analyzing the cumulative radiation exposure which has been registered as pits within a dosimeter track etch foil, comprising:
 a high intensity light source capable of generating a collimated beam of light along an optical path which impinges on the track etch foil of a dosimeter;
 a lens positioned along the optical path to collect and focus light exiting the track etch foil;
 an optical mask positioned on the optical path to block unscattered light which has exited the track etch foil; and
 an optical detector positioned along the optical path to register the optical power of the scattered light exiting the track etch foil, wherein the optical power of the scattered light is proportional to the number and size of the pits in the track etch foil according to Mie scattering at the point of impingement with said collimated beam of light and may be converted to a value of cumulative radiation exposure for the dosimeter, such as a value given in rems.

19. An apparatus as recited in claim 18, further comprising a holder for retaining said track etch foil along the optical path.

20. An apparatus as recited in claim 19, wherein said holder is configured to allow translational movements of the retained track etch foil when urged by a mechanical power source, wherein the translational movements of said track etch foil result in measurements being taken of scattered light which are averaged over an area of the track etch foil that exceed the area of the collimated beam.

21. An apparatus as recited in claim 20, further comprising a bar code reader attached to said holder, wherein the bar code reader is capable of reading a bar code from the track etch foil during movement of the track etch foil within the holder.

22. An apparatus as recited in claim 21, wherein said light source comprises a laser.

23. An apparatus as recited in claim 18, further comprising a telescopic lens positioned along the optical path which is capable of changing the diameter of the light beam directed at the track etch foil.

24. An apparatus as recited in claim 18, wherein said optical mask comprises a non-transparent target member positioned in the path of the unscattered beam of light.

25. A method for optically analyzing the cumulative radiation exposure of a dosimeter track etch foil, comprising:
 impinging a collimated high intensity light beam onto the surface of a track etch foil;
 masking out unscattered light from the impinging beam as it exits the track etch foil;
 collecting and measuring the optical-power of the light scattered by the track etch foil; and
 calculating a cumulative radiation exposure level which is proportional to the measured optical-power of the scattered light.

26. A method as recited in claim 25, wherein measuring the optical-power of the scattered light is performed by taking the sum of a weighted series of optical-power measurements, comprising:
 (a) calculating a radius of the distance from the center of the incoming light beam for each optical detector input power value;
 (b) determining a weighting factor for the given radius by calculating inverse tangents of each possible radius divided by a distance constant for the apparatus being used, and multiplying the result through a scattering angle weighting value arrived at according to the Mie scattering theory;
 (c) multiplying the weighting factor for the given radial distance by the sum of the optical power readings at the same radial distance to arrive at a radial power value;
 (d) adding the radial power value to a cumulative sum taken over the other radial distances; and
 (e) repeating steps (a) through (d) for each radial distance within the optical array, wherein the resultant cumulative sum taken over all radial distances equals the optical power of the received scattered light.

* * * * *